(12) United States Patent
Chen et al.

(10) Patent No.: US 10,415,785 B2
(45) Date of Patent: Sep. 17, 2019

(54) SUNLIGHT FOCUSING ANALYSIS DEVICE FOR VEHICLE LAMP LENS, AND METHOD FOR USING SAME

(71) Applicant: HASCO VISION TECHNOLOGY CO., LTD., Shanghai (CN)

(72) Inventors: Mingmin Chen, Shanghai (CN); Songjie Zhou, Shanghai (CN)

(73) Assignee: HASCO VISION TECHNOLOGY CO., LTD., Shanghai (CN)

( * ) Notice: Subject to any disclaimer, the term of this patent is extended or adjusted under 35 U.S.C. 154(b) by 0 days.

(21) Appl. No.: 16/095,293

(22) PCT Filed: Jul. 19, 2016

(86) PCT No.: PCT/CN2016/090386
§ 371 (c)(1),
(2) Date: Oct. 19, 2018

(87) PCT Pub. No.: WO2017/185534
PCT Pub. Date: Nov. 2, 2017

(65) Prior Publication Data
US 2019/0137067 A1    May 9, 2019

(30) Foreign Application Priority Data

Apr. 26, 2016  (CN) ................... 2016 1 0264609
Apr. 26, 2016  (CN) ................. 2016 2 0359664 U (51) Int. Cl.
| G01J 1/00 | (2006.01) |
| F21S 41/29 | (2018.01) |
| G01M 11/02 | (2006.01) |
| G01N 17/00 | (2006.01) |
| F21S 41/25 | (2018.01) |
| F24S 23/30 | (2018.01) |
| G01M 11/06 | (2006.01) |

(52) U.S. Cl.
CPC .............. *F21S 41/295* (2018.01); *F21S 41/25* (2018.01); *F24S 23/30* (2018.05); *G01M 11/02* (2013.01); *G01M 11/06* (2013.01); *G01N 17/00* (2013.01)

(58) Field of Classification Search
CPC ........ G01J 1/4257; G01J 9/00; G01M 11/061; G01M 11/064; G01M 11/06
USPC ........................................................ 356/121
See application file for complete search history.

(56) References Cited

U.S. PATENT DOCUMENTS

| 2011/0049992 A1* | 3/2011 | Sant'Anselmo | ........ H02S 10/10 307/64 |
| 2011/0316298 A1* | 12/2011 | Rampersad | ............ G06Q 30/02 296/21 |

* cited by examiner

Primary Examiner — Md M Rahman
(74) Attorney, Agent, or Firm — CBM Patent Consulting, LLC (57) ABSTRACT

A sunlight focusing analysis device relating to an analysis and verification device for a potential failure mode of a vehicle lamp projection unit, and a method for using same, and in particular to the analysis and verification of ablation of peripheral parts of a lens caused by focal spots formed by sunlight focused via a vehicle lamp lens. The device comprises a base, a lens holder, and a test piece holder. A horizontal rotary table and an inclination angle adjustment mechanism are provided on the base; the inclination angle adjustment mechanism is formed by a fixed support arm and a vertical swing arm connected to each other; the lens holder is fixed on the vertical swing arm; the test piece holder is mounted on a test piece lifting platform below the lens holder.

10 Claims, 8 Drawing Sheets

SUNLIGHT FOCUSING ANALYSIS DEVICE FOR VEHICLE LAMP LENS, AND METHOD FOR USING SAME

BACKGROUND OF THE INVENTION

Technical Field

The invention relates to an analysis and verification device for a potential failure mode of a vehicle lamp projection unit and a method for using same, in particular to the analysis and verification of ablation of peripheral parts of a lens caused by focal spots formed by sunlight focused via a vehicle lamp lens.

Description of Related Art

With the development of automotive lamps, projection units are increasingly applied to automotive headlamps to realize high and low beams. As an important constituent part of the projection units, lenses with different sizes and focal distances have been designed to meet different function and shape requirements. While the optical requirement has been met, an unexpected problem that peripheral parts of the lenses of the lamps are prone to ablation is fed back from the aftermarket. Through analysis, the reason for such ablation is that a high temperature in a small area is caused by focal spots formed on the peripheries of the lenses after sunlight is refracted and totally reflected by the lenses, consequentially, resulting in melting or ablation of the lamps and the peripheral plastic parts of the lamps.

The Chinese Invention Patent titled "Device for Measuring Dimension of Focal Spot of Optical Focusing System and Method for Using Same" (Invention Patent No. ZL201110352127.6, Authorization Publication No. CN10250715B) discloses a device for measuring the dimension of a focal spot of an optical focusing system and a method for using same. The device comprises a collimating laser light source, a reflection and transmission switching unit, a beam splitter mirror, a condensing mirror, a power detector, a first linear movement unit, a second linear movement unit, a double slit, a focusing lens, a CCD camera and a computer, wherein the collimating laser light source, the beam splitter mirror, the reflection and transmission switching unit, the double slit, the focusing lens and the CCD camera are sequentially arranged along the same optical path, the reflection and transmission switching unit is arranged on the first linear movement unit, the double slit and the focusing lens are arranged on the second linear movement unit, the condensing mirror and the power detector are sequentially arranged on a reflection optical path of the beam splitter mirror, the power detector, the first linear movement unit, the second linear movement unit and the CCD camera are all connected with the computer, and thus, the dimension of the focal spot is analyzed and measured.

However, ablation of the peripheral parts of the vehicle lens is accidentally caused by sunlight, deviating from a designed projection optical axis of the vehicle lens, focused by the vehicle lens outside the optical axis, and the ablated part and the degree of damage are random and depend on the parking direction of vehicles and the intensity of sunlight. The above-mentioned existing technical scheme for analyzing and measuring the focal spot formed by sunlight passing through the optical axis of the lens cannot be used for the observation, analysis and verification of ablation of automotive lamp parts around the lens caused by focused sunlight due to the fact that such scheme entirely fails to take focusing outside the optical axis of the vehicle lens into consideration.

BRIEF SUMMARY OF THE INVENTION

One objective of the invention is to provide a sunlight focusing analysis device, which is used for a vehicle lamp lens, can achieve reappearance and experimental verification of potential defects of vehicle lamps, according to the basic elements, such as sunlight energy, incident angles, and the distance between disabled parts and lenses, of damage caused by sunlight focused by different lenses, by comprehensively taking various focal spot ablation elements into consideration, and can rapidly obtain observation and analysis results under different light conditions through adjustable parts, thus, providing an effective technical means for the verification and analysis of the accidental failure design theory and actual examination of vehicle lamps.

The technical scheme adopted by the invention to solve the above-mentioned technical problems is as follows:

A sunlight focusing analysis device for a vehicle lamp lens comprises an adjustable horizontal base, a lens holder used to clamp a vehicle lamp lens, and a test piece holder used to hold a test piece. The sunlight focusing analysis device for a vehicle lamp lens is characterized in that a horizontal rotary table capable of rotating around a rotating shaft and an inclination angle adjustment mechanism arranged in the middle of the horizontal rotary table are provided on the base. The inclination angle adjustment mechanism is formed by a fixed support arm and a vertical swing arm connected to each other. The fixed support arm is fixedly connected to the horizontal rotary table. The vertical swing arm is rotatably connected to the fixed support arm through a swing arm shaft. The lens holder is fixed on the vertical swing arm. A center of the vehicle lamp lens is located at the intersection of an axis of the rotating shaft and an axis of the swing arm shaft. The test piece holder is mounted on a test piece lifting platform below the lens holder. The test piece lifting platform is fixedly mounted on the vertical swing arm and is used to adjust the distance between the test piece and the vehicle lamp lens. The test piece holder clamps and holds the test piece within a sunlight focusing observation area below the lens holder.

According to a better technical scheme of the sunlight focusing analysis device for a vehicle lamp lens, the test piece lifting platform comprises an X-type lifting structure provided with a height adjustment knob and a lifting platform height gauge used to read the height of the test piece. By adjusting the supporting height of the X-type lifting structure for the test piece holder, the longitudinal distance between the test piece and the vehicle lamp lens is changed, and then, changes of a sunlight focal spot along with changes of the longitudinal distance are observed and analyzed.

According to an improved technical scheme of the sunlight focusing analysis device for a vehicle lamp lens, a sunlight angle meter is arranged on the horizontal rotary table and is a ruler, which is provided with a pointer at the front end and is also provided with scale lines and a scale groove. The pointer is perpendicular to the horizontal rotary table. An axis of the pointer and a center line of the scale groove are parallel to a swinging surface of the swing arm of the inclination angle adjustment mechanism. When the horizontal rotary table is rotated to make the shadow of the pointer collinear with the scale groove, the sunlight focusing analysis device for a vehicle lamp lens is located at a position where sunlight can directly enter the sunlight focusing device, and the scale line to which the pointer points corresponds to the included angle α between the sunlight and the horizon. A swing arm inclination angle gauge is arranged on the inclination angle adjustment mechanism and is used to indicate a forward or backward swing arm inclination angle β of the test piece lifting platform around the swing arm shaft. A focal spot position measurement gauge parallel to the test piece is arranged on an edge of the test piece lifting platform and is used to read the transverse distance between the sunlight focal spot and the vehicle lamp lens. By adjusting the forward or backward swing arm inclination angle β of the test piece lifting platform around the swing arm shaft and the sunlight incidence angle γ of the vehicle lamp lens, the focal position of the vehicle lamp lens under different sunlight incidence angles γ can be observed and analyzed. Wherein, the sunlight incidence angle γ of the vehicle lamp lens is worked out according to a formula: γ=α+β.

According to an improved technical scheme of the sunlight focusing analysis device for a vehicle lamp lens, a bubble level is arranged on the horizontal rotary table, and three or four base bolts are arranged on the periphery of the base. By adjusting the supporting heights of the base bolts according to an indication of the bubble level, the horizontal rotary table is made in a horizontal state.

According to a further improved technical scheme of the sunlight focusing analysis device for a vehicle lamp lens, the lens holder is connected to the vertical swing arm in a double-station fixing manner. A lens holder body 90 can be locked on a first station to be parallel to the test piece 15 or can be locked on a second station to be perpendicular to the test piece 15.

According to a preferred technical scheme of the sunlight focusing analysis device for a vehicle lamp lens, the lens holder is of a three-jaw self-centering structure. Particularly, the vehicle lamp lens is clamped on the lens holder by means of three elastic lens holder jaws connected to the annular lens holder body, and a center line of the vehicle lamp lens is automatically aligned to an axis of the swing arm shaft.

According to another preferred technical scheme of the sunlight focusing analysis device for a vehicle lamp lens, the lens holder is of a four-jaw center-adjusting structure and is used to clamp a non-circular vehicle lamp lens. The lens holder body is provided with a circular sliding groove and four lens holder jaws which can move along the circular sliding groove or be locked on the circular sliding groove. By respectively adjusting the lock positions of the four lens holder jaws on the circular sliding groove, the non-circular vehicle lamp lens can be held by the lens holder, and the central position of the vehicle lamp lens is adjusted to be aligned to an axis of the swing arm shaft.

According to another improved technical scheme of the sunlight focusing analysis device for a vehicle lamp lens, the sunlight focusing analysis device further comprises a sunlight intensity meter used to measure the sunlight intensity. A probe of the sunlight intensity meter is fixed at a position, adjacent to the test piece, of the edge of the test piece lifting platform. The probe is in a direction parallel to the normal direction of the test piece.

Another objective of the invention is to provide a method for observing and analyzing a focal spot outside the optical axis of the vehicle lamp lens by means of the sunlight focusing analysis device for a vehicle lamp lens. The technical scheme adopted by the invention to solve the above-mentioned technical problems is as follows:

The method for observing and analyzing a focal spot outside the optical axis of the vehicle lamp lens by means of the sunlight focusing analysis device for the vehicle lamp lens is used for observing and analyzing a sunlight focal spot in front or below the vehicle lamp lens and comprises the following steps:

S10, a test piece used to simulate the shape and positional relation of a part and the vehicle lamp lens is prepared according to the material and surface treatment of the vehicle lamp peripheral part to be subjected to a focusing ablation analysis test, and the test piece is clamped by the test piece holder with a to-be-tested portion suspended, so that a test analysis result is prevented from being affected by heat conduction;

S20, the to-be-tested vehicle lamp lens is clamped on the lens holder with the lens holder body perpendicular to the test piece and the optical axis of the vehicle lamp lens parallel to the test piece;

S30, the horizontal rotary table of the sunlight focusing analysis device for a vehicle lamp lens is adjusted to the horizontal state;

S40, the horizontal rotary table is rotated to make the sunlight focusing analysis device for a vehicle lamp lens located at a position where sunlight can directly enter the sunlight focusing analysis device; then the horizontal rotary table is locked, and the included angle α between sunlight and the horizon is measured;

S50, the vertical swing arm is rotated according to the included angle α between sunlight and the horizon, the swing arm inclination angle β is measured at the same time, and the vertical swing arm is locked when the sunlight incidence angle γ of the vehicle lamp lens meets the focusing observation and analysis requirement: γ=α+β;

S60, the height of the test piece holder is adjusted to search for the minimum focal spot projected on the test piece after sunlight is focused via the vehicle lamp lens, and the longitudinal distance between the test piece and the vehicle lamp lens and the front-back distance between the focal spot and the lens are measured, so that the focal distance and focal position, outside the optical axis, of the tested vehicle lamp lens under the sunlight incidence angle γ are obtained;

S70, the height of the test piece holder is adjusted to change the height of the test piece with respect to the vehicle lamp lens and to change the size of the focal spot and the intensity of focal energy, and then, a focal spot range in which ablation of the test piece may be caused by sunlight focusing is measured; and S80, a sunlight intensity parameter is measured by means of the sunlight intensity meter and is used for focal energy analysis of sunlight focusing ablation of the vehicle lamp peripheral part.

According to an improved technical scheme of the method for observing and analyzing a focal spot outside the optical axis of a vehicle lamp lens, the method is used for observing and analyzing a sunlight focal spot behind the vehicle lamp lens and is characterized by further comprising the following steps between step S20 and step S30:

S22, installation of the lens holder is adjusted by rotating the lens holder by 90° to make the lens holder body parallel to the test piece and to make the optical axis of the vehicle lamp lens perpendicular to the test piece; and S24, the fixed position of the test piece holder on the test piece lifting platform is adjusted to move the test piece into a sunlight focusing observation area behind the vehicle lamp lens.

The invention has the following beneficial effects:

1. According to the sunlight focusing analysis device for a vehicle lamp lens and the method for using same, the horizontal rotary table and the inclination angle adjustment mechanism are used to drive the test piece and the vehicle lamp lens to implement 360° omni-directional rotation, so that a desired relative angle between the lens and sunlight can be obtained any time in the day when there is sunlight, and the focusing observation and analysis process is not affected by the actual altitude of the sun.

2. According to the sunlight focusing analysis device for a vehicle lamp lens and the method for using same, by rapidly adjusting the initial position of the device through the base bolts and the bubble level, the device can adapt to different platforms without being affected by the angles of the platforms; and the device can be adjusted through the horizontal rotary table and the sunlight angle meter to right faces sunlight, and thus, the whole device does not need to be moved in the whole focusing observation process.

3. According to the sunlight focusing analysis device for a vehicle lamp lens and the method for using same, lenses with different sizes and in different shapes can be clamped by the lens holder with the mounting position capable of being adjusted, so that different focusing observation, analysis and test requirement can be met.

Reference signs of all components in the figures: 1-base; 2-base bolt; 3-bubble level; 4-sunlight angle meter, 41-pointer, 42-scale line; 43-scale groove; 5-horizontal rotary table; 6-test piece lifting platform; 7-lifting platform height gauge; 8-height adjustment knob; 9-lens holder; 10-fixed support arm; 11-vertical swing arm; 12-swing arm inclination angle gauge; 13-swing arm shaft; 14-test piece holder; 15-test piece; 17-focal spot position measurement gauge; 18-rotating shaft; 20-sunlight intensity meter; 21-probe; 90-lens holder body; 91-vehicle lamp lens; 92-lens holder jaw.

DETAILED DESCRIPTION OF THE INVENTION

For a better understanding of the above technical scheme of the invention, the invention is further described in detail as follows in combination with the drawings and embodiments.

Figure 1:
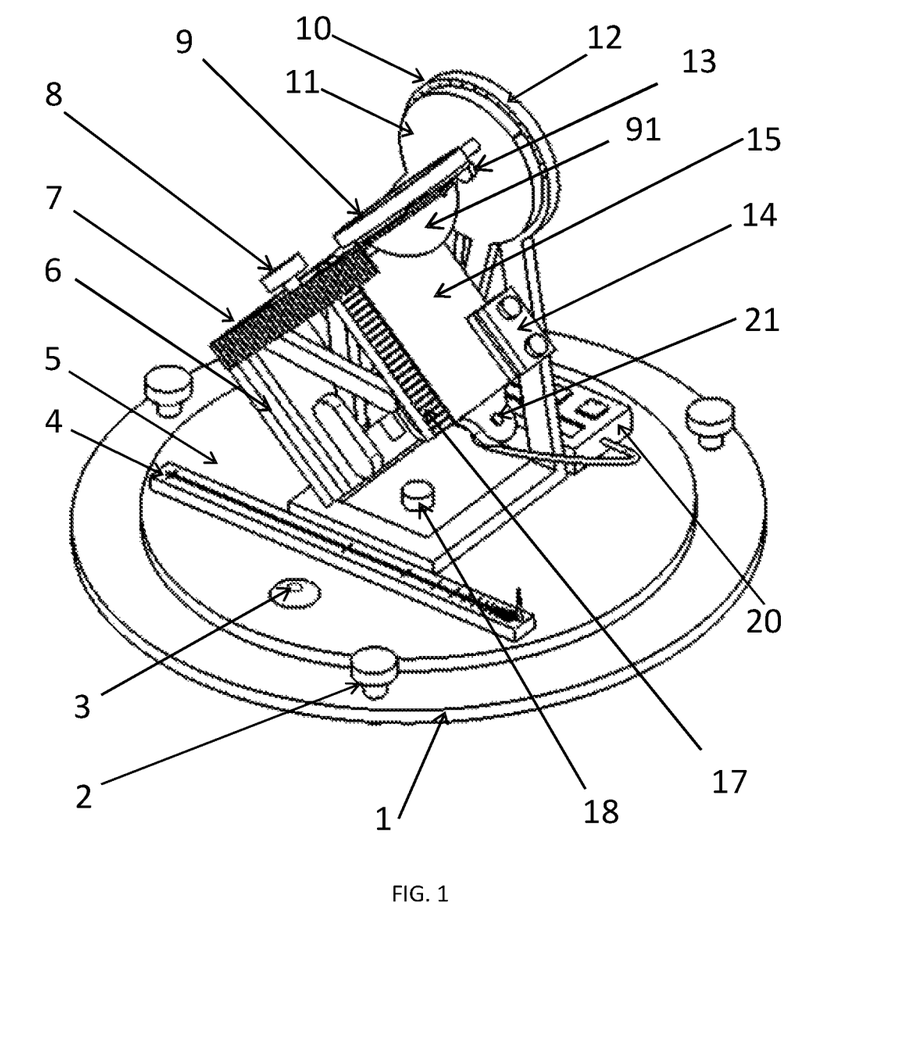
FIG. 1 is a structural view of the sunlight focusing analysis device for a vehicle lamp lens of the invention.
Figure 12:
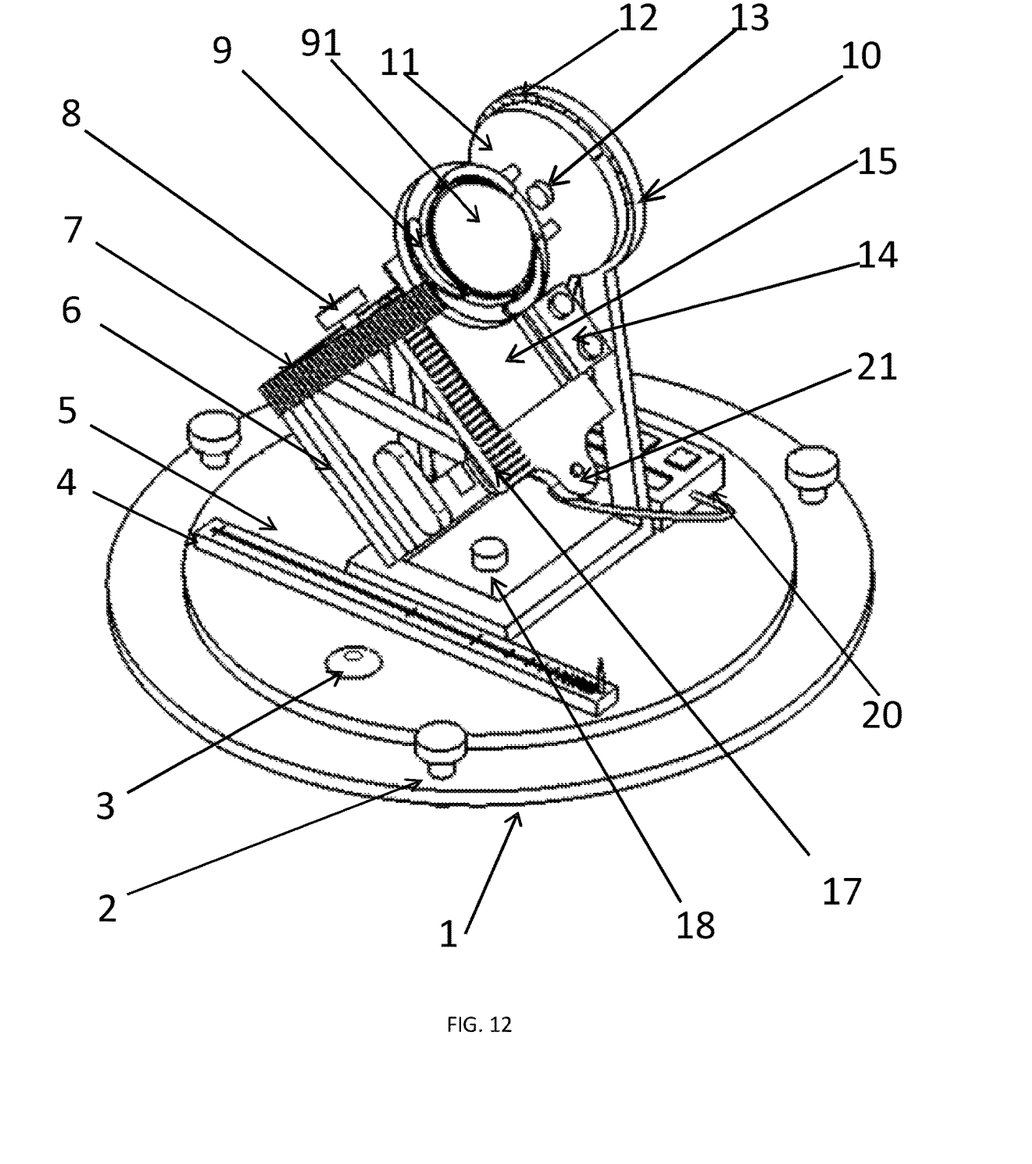
FIG. 12 is a diagram of observing a focal spot on the back of a lens by means of the sunlight focusing analysis device for a vehicle lamp lens of the invention.

As shown in FIG. 1 and FIG. 12, in one embodiment, the sunlight focusing analysis device for a vehicle lamp lens comprises an adjustable horizontal base 1, a lens holder 9 used to clamp a vehicle lamp lens 91, and a test piece holder 14 used to hold a test piece 15. A horizontal rotary table 5 capable of rotating around a rotating shaft 18 and an inclination angle adjustment mechanism arranged in the middle of the horizontal rotary table 5 are provided on the base 1. The inclination angle adjustment mechanism is formed by a fixed support arm 10 and a vertical swing arm 11 connected to each other. The fixed support arm 10 is fixedly connected to the horizontal rotary table 5. The vertical swing arm 11 is rotatably connected to the fixed support arm 10 through a swing arm shaft 13. The lens holder 9 is fixed on the vertical swing arm 11. A center of the vehicle lamp lens 91 is located at the intersection of an axis of the rotating shaft 18 and an axis of the swing arm shaft 13. By rotating the horizontal rotary table 5 and the vertical swing arm 11, a desired relative angle between the lens and sunlight can be obtained any time in the day when there is sunlight, without being affected by the actual altitude of the sun. The test piece holder 14 is mounted on a test piece lifting platform 6 below the lens holder 9. The test piece lifting platform 6 is fixedly mounted on the vertical swing arm 11 and is used to adjust the distance between the test piece 15 and the vehicle lamp lens 91. The test piece holder 14 clamps and holds the test piece 15 within a sunlight focusing observation area below the lens holder 9.

Figure 5:
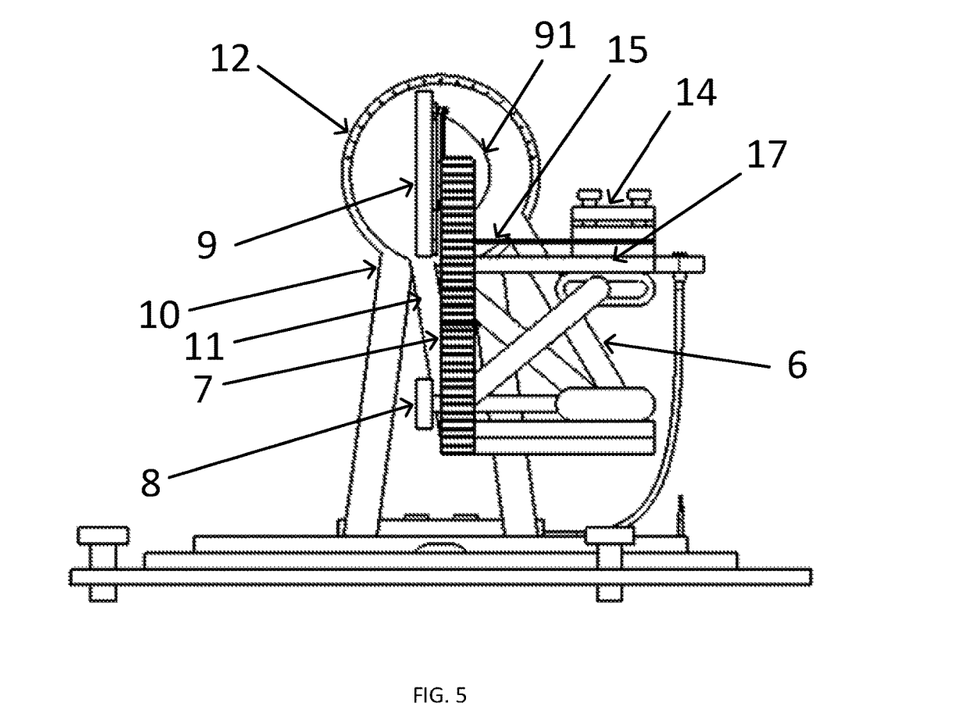
FIG. 5 is a side view when the sunlight focusing analysis device for a vehicle lamp lens is located at an initial position.
Figure 6:
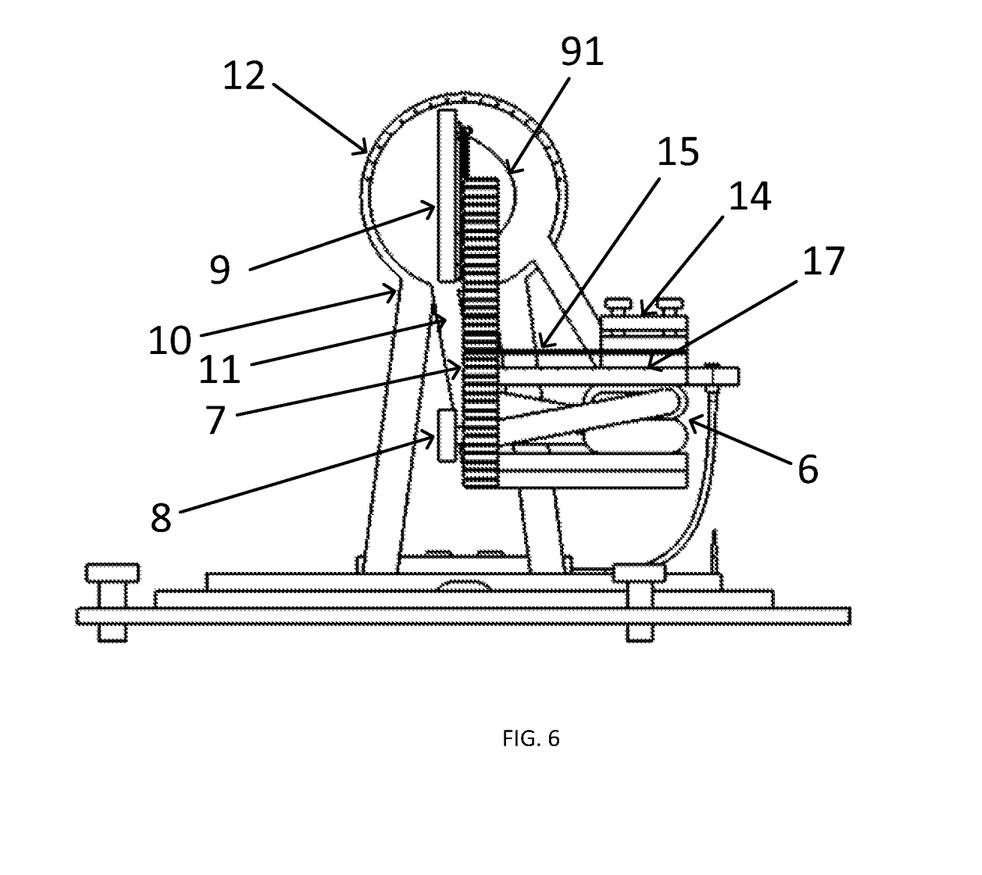
FIG. 6 is a side view when a test piece lifting platform of the sunlight focusing analysis device for a vehicle lamp lens is located at a lower position.

As shown in FIG. 1 and FIG. 12, in this embodiment of the sunlight focusing analysis device for a vehicle lamp lens, the test piece lifting platform 6 comprises an X-type lifting structure provided with a height adjustment knob 8 and a lifting platform height gauge 7 used to read the height of the test piece 15. By adjusting the supporting height of the X-type lifting structure for the test piece holder 14, the longitudinal distance between the test piece 15 and the vehicle lamp lens 91 is changed, and then, changes of a sunlight focal spot along with changes of the longitudinal distance are observed and analyzed, as shown in FIG. 5 and FIG. 6.

Figure 2:
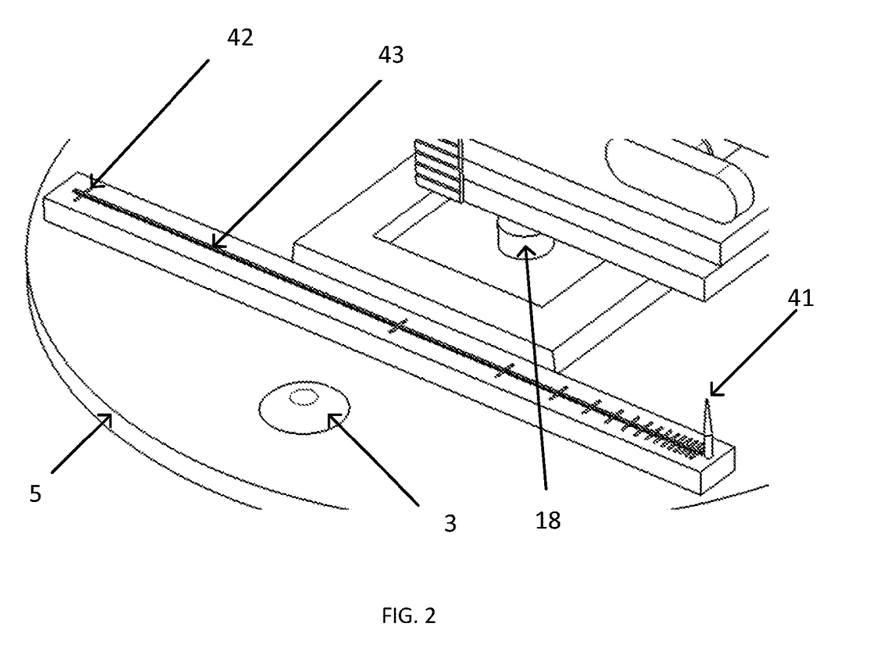
FIG. 2 is a structural view of a sunlight angle meter of the sunlight focusing analysis device for a vehicle lamp lens.
Figure 3:
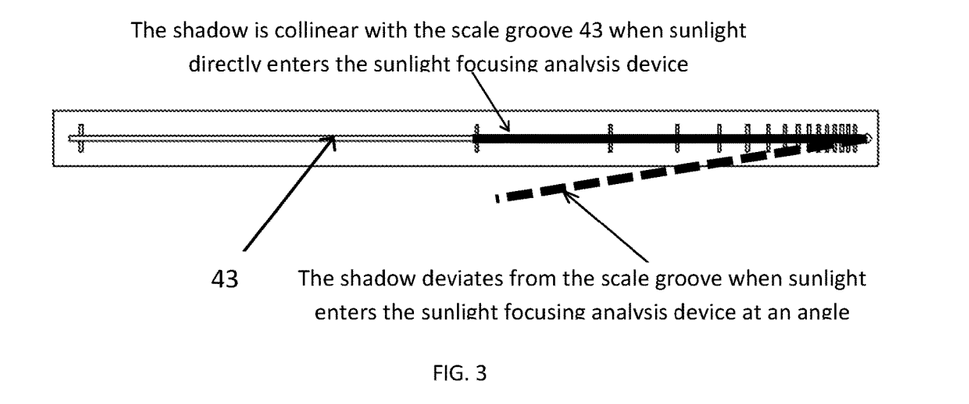
FIG. 3 is a diagram of adjusting the sunlight incidence direction by means of the sunlight angle meter.
Figure 4:
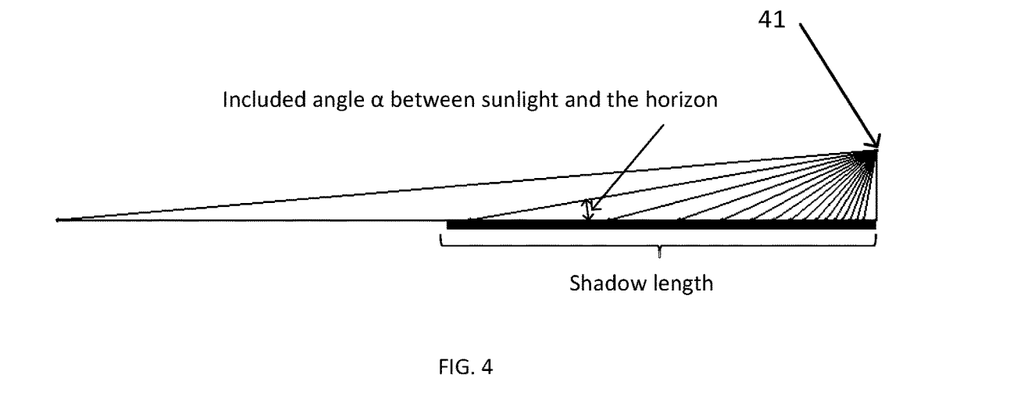
FIG. 4 is a diagram of measuring an included angle between sunlight and the horizon by means of the sunlight angle meter.
Figure 7:
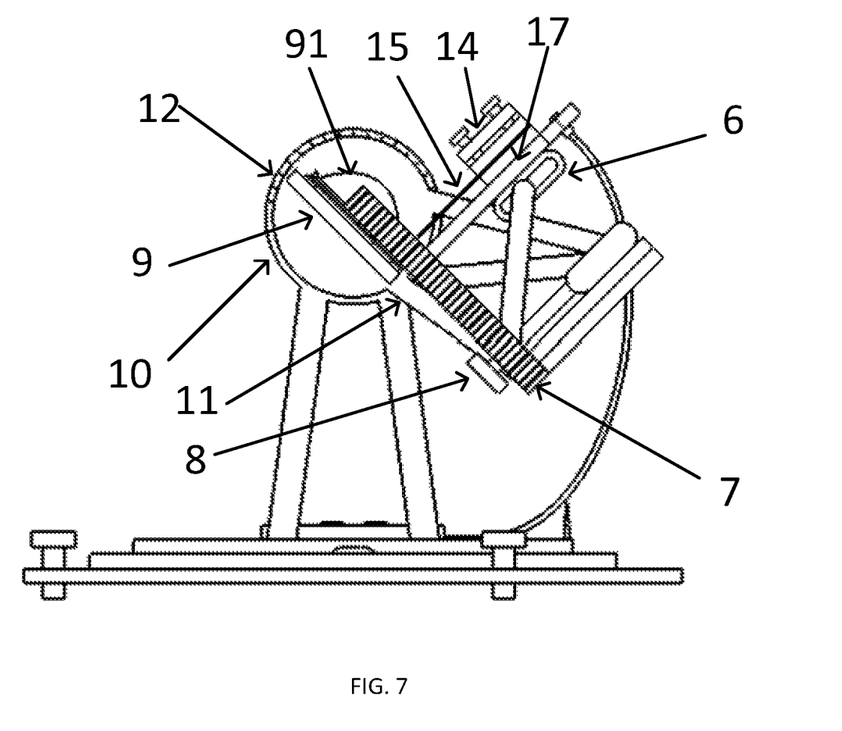
FIG. 7 is a side view when the sunlight focusing analysis device for a vehicle lamp lens inclines backwards.
Figure 8:
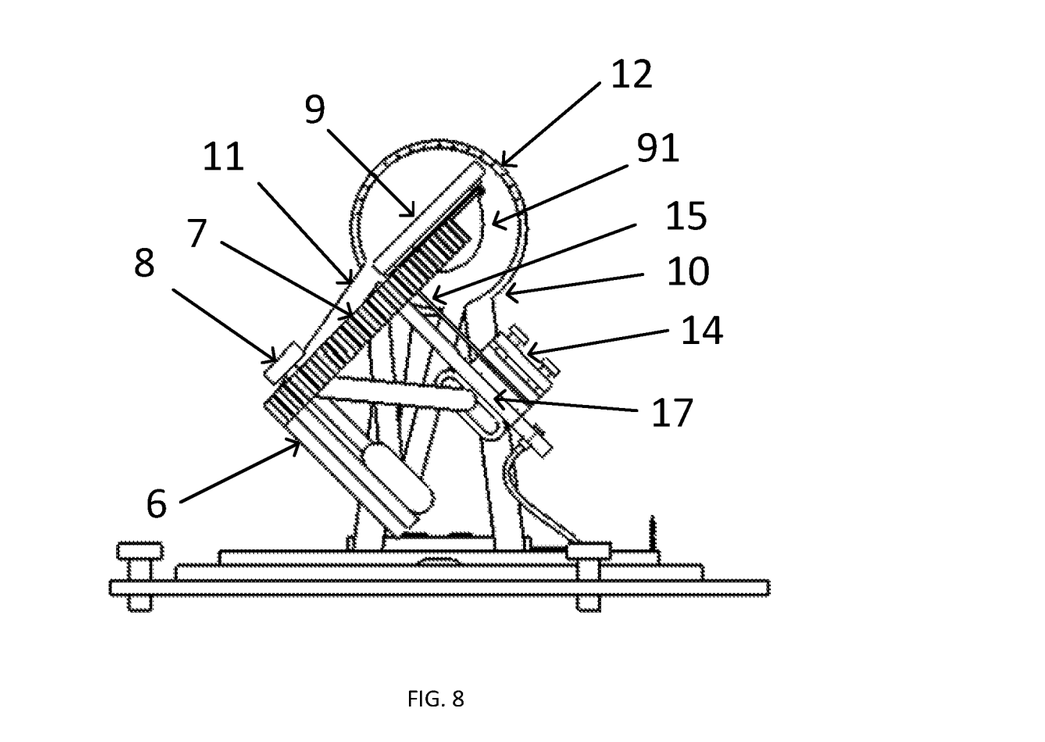
FIG. 8 is a side view when the sunlight focusing analysis device for a vehicle lamp lens inclines forwards.
Figure 9:
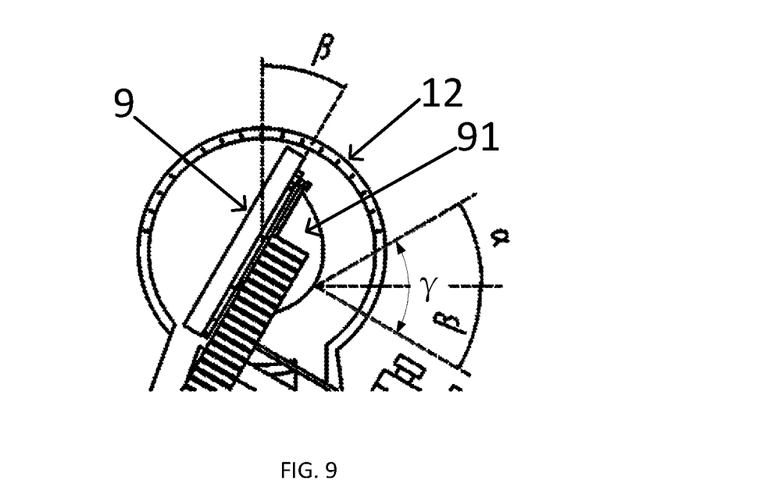
FIG. 9 is a principle diagram of determining the sunlight incidence angle according to a rotation angle of the test piece lifting platform.

As shown in FIG. 1 and FIG. 12, in this embodiment of the sunlight focusing analysis device for a vehicle lamp lens, a sunlight angle meter 4 is arranged on the horizontal rotary table 5 and is a ruler, which is provided with a pointer 41 at the front end and is also provided with scale lines 42 and a scale groove 43. The pointer 41 is perpendicular to the horizontal rotary table 5. An axis of the pointer 41 and a center line of the scale groove 43 are parallel to a swinging surface of the swing arm of the inclination angle adjustment mechanism. The scale lines 42 are carved according to the relation of the included angle α between sunlight and the horizon to the projection length of the pointer 41. When the horizontal rotary table 5 is rotated to make the shadow of the pointer 41 collinear with the scale groove 43, the sunlight focusing analysis device for a vehicle lamp lens is located at a position where sunlight can directly enter the sunlight focusing device, and the scale lines 42 to which the pointer 41 points corresponds to the included angle α between the sunlight and the horizon, as shown in FIGS. 2-4. A swing arm inclination angle gauge 12 is arranged on the inclination angle adjustment mechanism and is used to indicate a forward or backward swing arm inclination angle β of the test piece lifting platform 6 around the swing arm shaft 13. A focal spot position measurement gauge 17 parallel to the test piece 15 is arranged on an edge of the test piece lifting platform 6 and is used to read the transverse distance between the sunlight focal spot and the vehicle lamp lens 91. By adjusting the forward or backward swing arm inclination angle β of the test piece lifting platform 6 around the swing arm shaft 13 and the sunlight incidence angle γ of the vehicle lamp lens 91, the focal position of the vehicle lamp lens 91 under different sunlight incidence angles γ can be observed and analyzed. Wherein, the sunlight incidence angle γ of the vehicle lamp lens 91 is worked out according to a formula: γ=α+β, as shown in FIGS. 7-9.

As shown in FIG. 1 and FIG. 12, in this embodiment of the sunlight focusing analysis device for a vehicle lamp lens, a bubble level 3 is arranged on the horizontal rotary table 5, and three or four base bolts 2 are arranged on the periphery of the base 1. By adjusting the supporting heights of the base bolts 2 according to an indication of the bubble level 3, the horizontal rotary table 5 is made in a horizontal state.

As shown in FIG. 1 and FIG. 12, in this embodiment of the sunlight focusing analysis device for a vehicle lamp lens, the lens holder 9 is connected to the vertical swing arm 11 in a double-station fixing manner. A lens holder body 90 can be locked on a first station to be parallel to the test piece 15 or can be locked on a second station to be perpendicular to the test piece 15.

Figure 10:
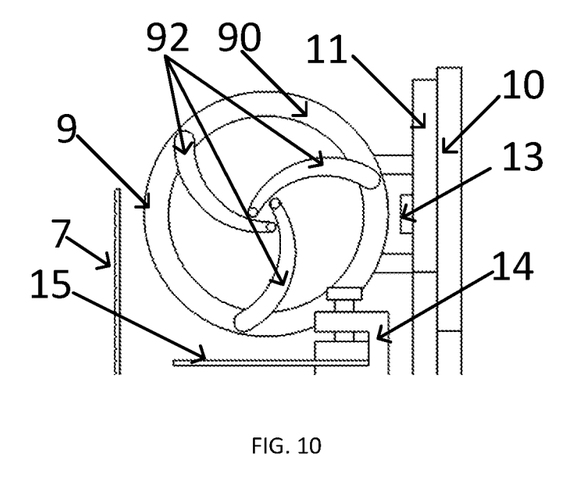
FIG. 10 is a structural view of a lens holder of the sunlight focusing analysis device for a vehicle lamp lens of the invention.
Figure 11:
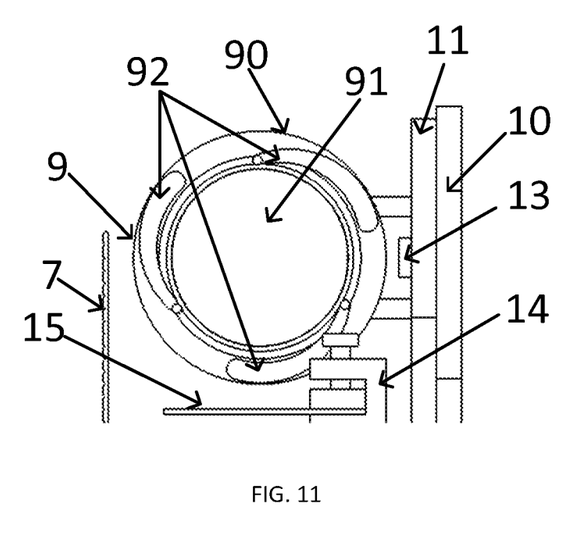
FIG. 11 is a diagram of a state where the lens holder of the sunlight focusing analysis device for a vehicle lamp lens clamps a lens.

As shown in FIG. 10 and FIG. 11, in another embodiment of the sunlight focusing analysis device for a vehicle lamp lens, the lens holder 9 is of a three-jaw self-centering structure. Particularly, the vehicle lamp lens 91 is clamped on the lens holder 9 by means of three elastic lens holder jaws 92 connected to the annular lens holder body 90, and a center line of the vehicle lamp lens 91 is automatically aligned to an axis of the swing arm shaft 13.

In another embodiment of the sunlight focusing analysis device for a vehicle lamp lens, the lens holder 9 is of a four-jaw center-adjusting structure and is used to clamp a non-circular vehicle lamp lens (not shown). The lens holder body 90 is provided with a circular sliding groove and four lens holder jaws which can move along the circular sliding groove or be locked on the circular sliding groove. By respectively adjusting the lock positions of the four lens holder jaws on the circular sliding groove, the non-circular vehicle lamp lens can be held by the lens holder, and the central position of the vehicle lamp lens is adjusted to be aligned to an axis of the swing arm shaft 13.

As shown in FIG. 1 and FIG. 12, in this embodiment of the sunlight focusing analysis device for a vehicle lamp lens, the sunlight focusing analysis device further comprises a sunlight intensity meter 20 used to measure the sunlight intensity. A probe 21 of the sunlight intensity meter 20 is fixed at a position, adjacent to the test piece 15, of the edge of the test piece lifting platform 6. The probe 21 is in a direction parallel to the normal direction of the test piece 15, so that it is ensured that the sunlight intensity received by the probe 21 is consistent with the sunlight intensity in the sunlight focusing observation area.

In one embodiment, a method for observing and analyzing a focal spot outside the optical axis of the vehicle lamp lens by means of the sunlight focusing analysis device for the vehicle lamp lens is used for observing and analyzing a sunlight focal spot in front or below the vehicle lamp lens and comprises the following steps:

S10, a test piece 15 used to simulate the shape and positional relation of a part and the vehicle lamp lens 91 is prepared according to the material and surface treatment of the vehicle lamp peripheral part to be subjected to a focusing ablation analysis test, and the test piece 15 is clamped by the test piece holder 14 with a to-be-tested portion suspended, so that a test analysis result is prevented from being affected by heat conduction;

S20, the to-be-tested vehicle lamp lens 91 is clamped on the lens holder 9 with the lens holder body 90 perpendicular to the test piece 15 and the optical axis of the vehicle lamp lens 91 parallel to the test piece;

S30, the supporting heights of the three base bolts 2 are adjusted according to the indication of the bubble level 3, so that the horizontal rotary table 5 of the sunlight focusing analysis device for a vehicle lamp lens is adjusted to the horizontal state;

S40, the horizontal rotary table 5 is rotated to make the shadow of the pointer 41 of the sunlight angle meter 4 collinear with the scale groove 43 and to make the sunlight focusing analysis device for a vehicle lamp lens located at a position where sunlight can directly enter the sunlight focusing analysis device, and then the horizontal rotary table 5 is locked; and the included angle α between sunlight and the horizon is directed read according to the corresponding scale lines 42;

S50, the vertical swing arm 11 is forwards or backwards rotated around the swing arm shaft 13 according to the included angle α between sunlight and the horizon, the swing arm inclination angle β is read at the same time, and the vertical swing arm 11 is locked when the sunlight incidence angle γ of the vehicle lamp lens 91 meets the focusing observation and analysis requirement: γ=α+β;

S60, the height of the test piece holder 14 is adjusted to search for the minimum focal spot projected on the test piece 15 after sunlight is focused via the vehicle lamp lens 91, and the longitudinal distance between the test piece 15 and the vehicle lamp lens 91 is read by means of the lifting platform height gauge 7; afterwards, the front-back distance between the focal spot and the lens is read by means of the focal spot position measurement gauge 17, so that the focal distance and focal position, outside the optical axis, of the tested vehicle lamp lens 91 under the sunlight incidence angle γ are obtained;

S70, by adjusting the height adjustment knob 8, the height of the test piece holder 14 is adjusted to change the height of the test piece 15 with respect to the vehicle lamp lens 91 and to change the size of the focal spot and the intensity of focal energy, and then, a focal spot range in which ablation of the test piece may be caused by sunlight focusing is measured; and S80, the intensity of sunlight is measured by the probe 21 fixed on the test piece lifting platform, and a sunlight intensity parameter is read by means of the sunlight intensity meter 20 and is used for focal energy analysis of sunlight focusing ablation of the vehicle lamp peripheral part.

In another embodiment of the method for observing and analyzing the focal spot outside the optical axis of the vehicle lamp lens, the method is used for observing and analyzing a sunlight focal spot behind the vehicle lamp lens and further comprises the following steps between step S20 and step S30:

S22, installation of the lens holder 9 is adjusted by rotating the lens holder 9 by 90° to make the lens holder body 90 parallel to the test piece and to make the optical axis of the vehicle lamp lens 91 perpendicular to the test piece 15; and S24, the fixed position of the test piece holder 14 on the test piece lifting platform 6 is adjusted to move the test piece into a sunlight focusing observation area behind the vehicle lamp lens.

In this embodiment, when the sunlight incidence angle γ of the vehicle lamp lens 91 is adjusted to 90°, the sunlight incidence direction coincides with the optical axis of the vehicle lamp lens 91, and thus, the sunlight focusing analysis device for a vehicle lamp lens can also be used for observation and analysis of focal spots on the optical axis of the vehicle lamp lens.

Those ordinarily skilled in this field would appreciate that the above embodiments are only used for explaining the technical scheme of the invention and are not used for limiting the invention. Any variations and modifications of the embodiments based on the essential spirit of the invention should fall within the protection scope of the claims of the invention.

What is claimed is:

1. A sunlight focusing analysis device for a vehicle lamp lens, comprising an adjustable horizontal base, a lens holder used to clamp a vehicle lamp lens, and a test piece holder used to hold a test piece, wherein a horizontal rotary table capable of rotating around a rotating shaft and an inclination angle adjustment mechanism arranged in a middle of the horizontal rotary table are provided on the base, the inclination angle adjustment mechanism is formed by a fixed support arm and a vertical swing arm connected to each other, the fixed support arm is fixedly connected to the horizontal rotary table, and the vertical swing arm is rotatably connected to the fixed support arm through a swing arm shaft; the lens holder is fixed on the vertical swing arm, a center of the vehicle lamp lens is located at an intersection of an axis of the rotating shaft and an axis of the swing arm shaft, the test piece holder is mounted on a test piece lifting platform below the lens holder, the test piece lifting platform is fixedly mounted on the vertical swing arm and is used to adjust a distance between the test piece and the vehicle lamp lens, and the test piece holder clamps and holds the test piece within a sunlight focusing observation area below the lens holder.

2. The sunlight focusing analysis device for a vehicle lamp lens according to claim 1, wherein the test piece lifting platform comprises an X-type lifting structure provided with a height adjustment knob and a lifting platform height gauge used to read a height of the test piece; and by adjusting a supporting height of the X-type lifting structure for the test piece holder, a longitudinal distance between the test piece and the vehicle lamp lens is changed, and then, changes of a sunlight focal spot along with changes of the longitudinal distance are observed and analyzed.

3. The sunlight focusing analysis device for a vehicle lamp lens according to claim 1, wherein a sunlight angle meter is arranged on the horizontal rotary table; the sunlight angle meter is a ruler which has a front end provided with a pointer and is provided with scale lines and a scale groove, the pointer is perpendicular to the horizontal rotary table, and an axis of the pointer and a center line of the scale groove are parallel to a swinging surface of the swing arm of the inclination angle adjustment mechanism; when the horizontal rotary table is rotated to make a shadow of the pointer collinear with the scale groove, the sunlight focusing analysis device for a vehicle lamp lens is located at a position where sunlight directly enters the sunlight focusing device, and the scale line to which the pointer points corresponds to an included angle α between the sunlight and the horizon; a swing arm inclination angle gauge is arranged on the inclination angle adjustment mechanism and is used to indicate a forward or backward swing arm inclination angle β of the test piece lifting platform around the swing arm shaft; a focal spot position measurement gauge parallel to the test piece is arranged on an edge of the test piece lifting platform and is used to read a transverse distance between the sunlight focal spot and the vehicle lamp lens; and by adjusting the forward or backward swing arm inclination angle β of the test piece lifting platform around the swing arm shaft and a sunlight incidence angle γ of the vehicle lamp lens, a focal position of the vehicle lamp lens under different sunlight incidence angles γ is observed and analyzed; wherein, the sunlight incidence angle γ of the vehicle lamp lens is worked out according to a formula: γ=α+β.

4. The sunlight focusing analysis device for a vehicle lamp lens according to claim 1, wherein three or four base bolts are arranged on a periphery of the base, and a bubble level is arranged on the horizontal rotary table; and by adjusting supporting heights of the base bolts according to an indication of the bubble level, the horizontal rotary table is made in a horizontal state.

5. The sunlight focusing analysis device for a vehicle lamp lens according to claim 1, wherein the lens holder is connected to the vertical swing arm in a double-station fixing manner, and particularly, a lens holder body 90 is locked on a first station to be parallel to the test piece 15 or is locked on a second station to be perpendicular to the test piece 15.

6. The sunlight focusing analysis device for a vehicle lamp lens according to claim 1, wherein the lens holder is of a three-jaw self-centering structure; and particularly, the vehicle lamp lens is clamped on the lens holder by means of three elastic lens holder jaws connected to an annular lens holder body, and a center line of the vehicle lamp lens is automatically aligned to an axis of the swing arm shaft.

7. The sunlight focusing analysis device for a vehicle lamp lens according to claim 1, wherein the lens holder is of a four-jaw center-adjusting structure and is used to clamp a non-circular vehicle lamp lens; a lens holder body is provided with a circular sliding groove and four lens holder jaws capable of moving along the circular sliding groove or being locked on the circular sliding groove; and by respectively adjusting lock positions of the four lens holder jaws on the circular sliding groove, the non-circular vehicle lamp lens is held by the lens holder, and a central position of the vehicle lamp lens is adjusted to be aligned to an axis of the swing arm shaft.

8. The sunlight focusing analysis device for a vehicle lamp lens according to claim 1, wherein the sunlight focusing analysis device further comprises a sunlight intensity meter used to measure a sunlight intensity, a probe of the sunlight intensity meter is fixed at a position, adjacent to the test piece, of an edge of the test piece lifting platform, and the probe is in a direction parallel to a normal direction of the test piece.

9. A method for observing and analyzing a focal spot outside an optical axis of a vehicle lamp lens by means of the sunlight focusing analysis device for a vehicle lamp lens according to claim 1, used for observing and analyzing a sunlight focal spot in front or below the vehicle lamp lens, comprising the following steps:

S10, preparing a test piece used to simulate a shape and positional relation of a part and the vehicle lamp lens according to the material and surface treatment of the vehicle lamp peripheral part to be subjected to a focusing ablation analysis test, and clamping, by the test piece holder, the test piece with a to-be-tested portion suspended, so that a test analysis result is prevented from being affected by heat conduction;

S20, clamping, by the lens holder, the to-be-tested vehicle lamp lens with the lens holder body perpendicular to the test piece and the optical axis of the vehicle lamp lens parallel to the test piece;

S30, adjusting the horizontal rotary table of the sunlight focusing analysis device for a vehicle lamp lens to the horizontal state;

S40, rotating the horizontal rotary table to make the sunlight focusing analysis device for a vehicle lamp lens located at a position where sunlight directly enters the sunlight focusing analysis device, then, locking the horizontal rotary table, and measuring the included angle $\alpha$ between the sunlight and the horizon;

S50, rotating the vertical swing arm according to the included angle $\alpha$ between sunlight and the horizon, measuring the swing arm inclination angle $\beta$ at the same time, and locking the vertical swing arm when the sunlight incidence angle $\gamma$ of the vehicle lamp lens meets a focusing observation and analysis requirement: $\gamma=\alpha+\beta$;

S60, adjusting a height of the test piece holder to search for the minimum focal spot projected on the test piece after the sunlight is focused via the vehicle lamp lens, and measuring the longitudinal distance between the test piece and the vehicle lamp lens and the front-back distance between the focal spot and the lens, so that a focal distance and focal position, outside the optical axis, of the tested vehicle lamp lens under the sunlight incidence angle $\gamma$ are obtained;

S70, adjusting the height of the test piece holder to change a height of the test piece with respect to the vehicle lamp lens and to change a size of the focal spot and an intensity of focal energy, and then measuring a focal spot range in which ablation of the test piece may be caused by sunlight focusing; and S80, measuring, by the sunlight intensity meter, a sunlight intensity parameter used for focal energy analysis of sunlight focusing ablation of the vehicle lamp peripheral part.

10. The method for observing and analyzing a focal spot outside an optical axis of a vehicle lamp lens according to claim 9, used for observing and analyzing a sunlight focal spot behind a vehicle lamp lens, further comprising the following steps between step S20 and step S30:

S22, adjusting installation of the lens holder by rotating the lens holder by 90° to make the lens holder body parallel to the test piece and to make the optical axis of the vehicle lamp lens perpendicular to the test piece; and S24, adjusting a fixed position of the test piece holder on the test piece lifting platform to move the test piece into a sunlight focusing observation area behind the vehicle lamp lens.

* * * * *